(12) United States Patent
Trinkaus et al.

(10) Patent No.: US 7,391,026 B2
(45) Date of Patent: Jun. 24, 2008

(54) PREPARATION OF A SELECTION OF CONTROL VARIABLES FOR A DOSE DISTRIBUTION TO BE ADJUSTED IN A TECHNICAL APPLIANCE

(75) Inventors: Hans Trinkaus, Kaiserslautern (DE); Karl-Heinz Kuefer, Weilerbach (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 171 days.

(21) Appl. No.: 10/493,501

(22) PCT Filed: Oct. 21, 2002

(86) PCT No.: PCT/DE02/03969

§ 371 (c)(1),
(2), (4) Date: Nov. 22, 2004

(87) PCT Pub. No.: WO03/038725

PCT Pub. Date: May 8, 2003

(65) Prior Publication Data

US 2005/0116172 A1 Jun. 2, 2005

(30) Foreign Application Priority Data

Oct. 22, 2001 (DE) ................................. 101 51 987

(51) Int. Cl.
*G01T 1/161* (2006.01)
(52) U.S. Cl. ..................... 250/363.02; 378/65; 378/153; 600/427
(58) Field of Classification Search ............ 250/363.02; 378/64, 65, 153, 54; 600/427
See application file for complete search history.

(56) References Cited

U.S. PATENT DOCUMENTS 5,418,827 A * 5/1995 Deasy et al. .................. 378/65

(Continued)

OTHER PUBLICATIONS

Hamacher et al. "Inverse radiation therapy planning-a multiple objective optimisation approach", Technical Report (ITWM), pp. 10-14, Dec. 1999.*

(Continued)

*Primary Examiner*—Christine Sung
(74) *Attorney, Agent, or Firm*—Foley & Lardner LLP

(57) ABSTRACT

The invention relates to a planning tool for the interactive selection of control variables ($x_1$, $y_7$, $\alpha_1$, $\alpha_2$, $\alpha_3$, $I_1$, $I_2$) of a radiation therapy plan from a database (1) comprising a plurality of pre-calculated solutions. Each solution represents a radiation therapy plan which, from a technical point of view, consists of a plurality of control variables or instructions. Each solution also has characteristic values for radiation doses for a target volume (T, Target) and at least one risk volume (risk organ, $h_1$, $h_2$, $h_3$) which are stored in the database (1). A plurality of axes are visibly represented on a display device (3; 3a, 3b) as radiation dose scales (30, 31, 32, 33) for the target volume (T) and the at least one risk volume ($h_1$, $h_2$, $h_3$), for the formation of at least one risk axis and one target axis. The characteristic values (50, 51, 52, 53) of the radiation doses for at least a plurality of the stored solutions are allocated to the respective corresponding axes in such a way that an acceptance interval ($a_{30}$, $a_{31}$, $a_{32}$, $a_{33}$) is created for each risk axis (31, 32, 33) and the target axis (30), said acceptance interval determining a common planning area (40; 41, 42) for all axes. Said planning area (40) is visibly emphasised on the display device (3) in relation to the surrounding field (45, 45a).

50 Claims, 8 Drawing Sheets
(1 of 8 Drawing Sheet(s) Filed in Color)

U.S. PATENT DOCUMENTS

| | | | | |
|---|---|---|---|---|
| 5,528,650 | A | * | 6/1996 | Swerdloff et al. ............. 378/65 |
| 5,602,892 | A | * | 2/1997 | Llacer ......................... 378/65 |
| 5,663,999 | A | | 9/1997 | Siochi |
| 6,222,905 | B1 | | 4/2001 | Yoda et al. |
| 6,512,942 | B1 | * | 1/2003 | Burdette et al. ............. 600/427 |
| 6,560,311 | B1 | * | 5/2003 | Shepard et al. ............... 378/65 |
| 7,027,557 | B2 | * | 4/2006 | Llacer ......................... 378/65 |
| 2004/0030227 | A1 | * | 2/2004 | Littrup et al. ............... 600/300 |
| 2005/0254622 | A1 | * | 11/2005 | Llacer ......................... 378/65 |

OTHER PUBLICATIONS

Ehrgott et al. "Radiation therapy planning by multicriteria optimisation".*

K. Preiser et al., "A New Program For Inverse Radiotherapy Planning", XIIth ICCR May 27-30, 1997, Salt Lake City Utah USA, pp. 425-428.

Thomas Bortfeld et al., "Clinically Relevant Intensity Modulation Optimization Using Physic Criteria", XIIth ICCR May 27-30, 1997, Salt Lake City Utah, USA, pp. 1-4.

Hamacher, H. W., "Inverse radiation therapy planning—a multiple objective optimization approach", Technical Report (ITWM), pp. 1-14 (Dec. 1999).

Arellano, A. R., et al., "Clinically oriented inverse planning implementation" Proceedings of the 22$^{nd}$ Annual International Conference of the IEEE Engineering In Medicine and Biology Society (Cat. No. 00CH37143), Proceedings of the 22$^{nd}$ Annual International Conference of the Engineering in Medicine and Biology Society, Chic, vol. 3, pp. 2071-2074 (2000).

Küfer, K. H., "A multicriteria optimization approach for inverse radiotherapy planning", Operations Research Proceedings, pp. 3-7 (Sep. 2000).

Qiuwen, Wu et al., "IMRT optimization based on the generalized equivalent uniform dose (EUD)", Proceeding sof the 22$^{nd}$ Annual International Conference of the IEEE Engineering in Medicine and Biology Society (Cat. No. 00CH37143), Proceedings of the 22$^{nd}$ Annual International Conference of the IEEE Engineering in Medicine and Biology Society, Chic, vol. 1, pp. 710-713 (2000).

Censor, Y: "Mathematical aspects of radiation therapy treatment planning: continuous inversion versus full discretization and optimization versus feasibility", Computational Radiology and Imaging: Therapy and Diagnostics, Bd. 110, pp. 1-12 (1999).

K. Preiser et al., "A New Program for Inverse Radiotherapy Planning", Xllth ICCR May 27-30, 1997, Salt Lake City, Utah U.S.A., pp. 425-428.

Thomas Bortfeld et al., "Clinically Relevant Intensity Modulation Optimization Using Physic Criteria", Xllth ICCR May 27-30, 1997, Salt Lake City, Utah, U.S.A., pp. 1-4.

* cited by examiner

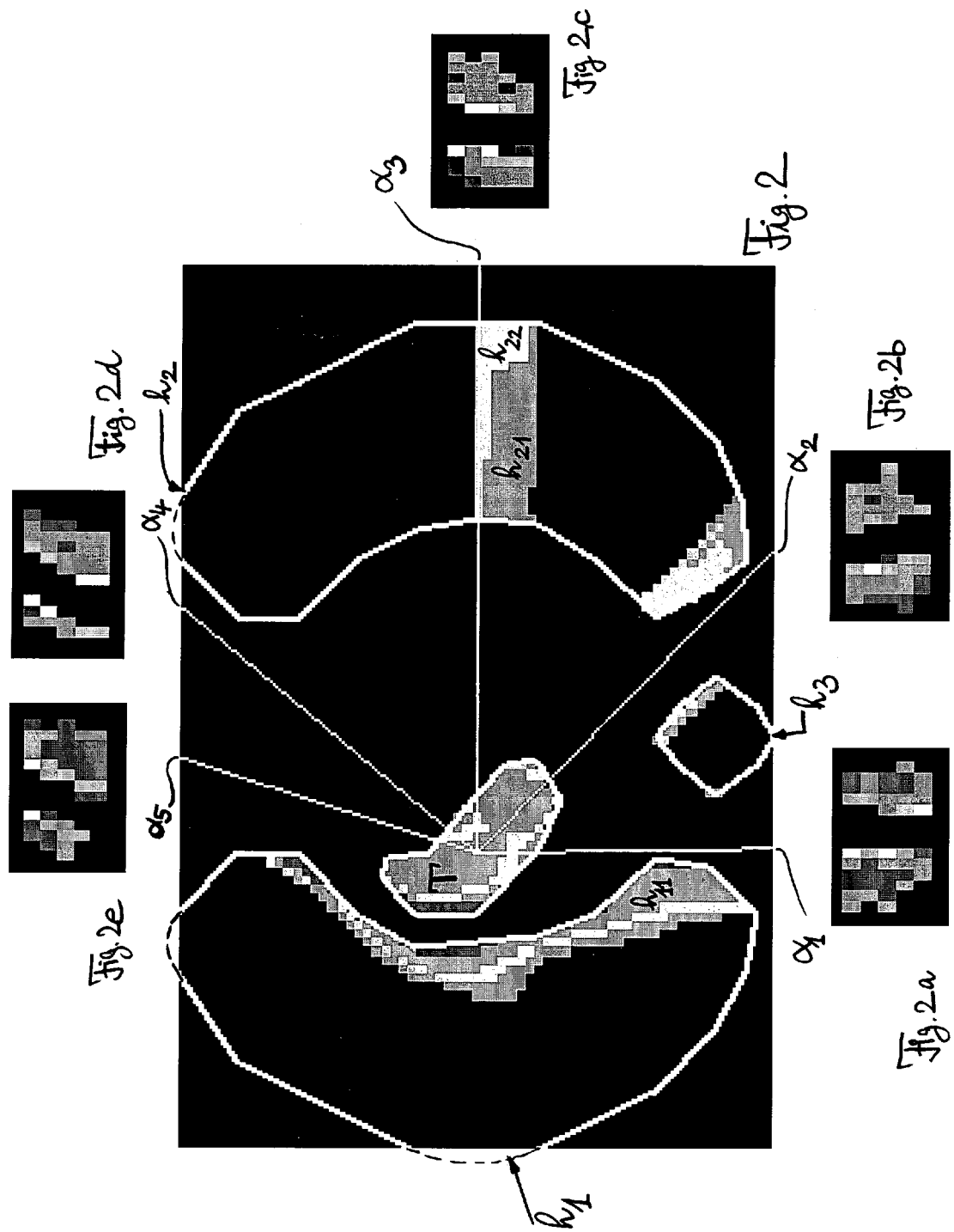

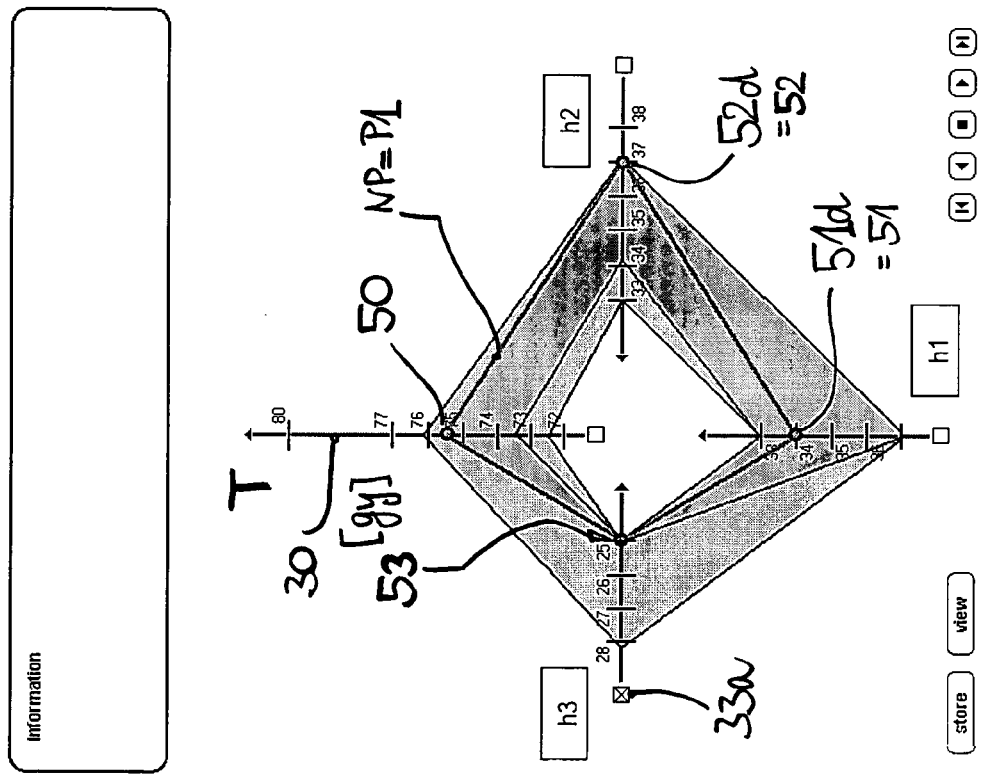
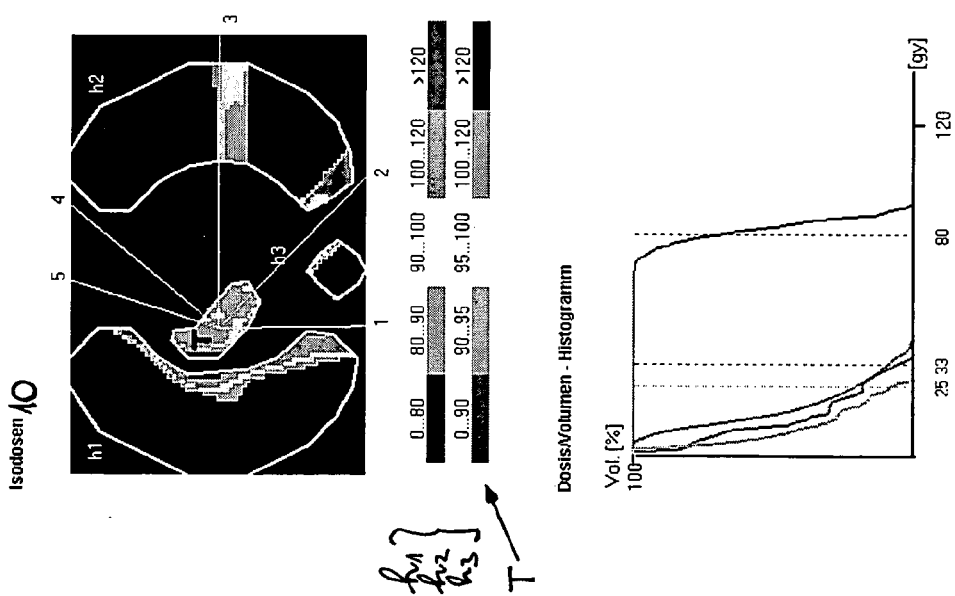

PREPARATION OF A SELECTION OF CONTROL VARIABLES FOR A DOSE DISTRIBUTION TO BE ADJUSTED IN A TECHNICAL APPLIANCE

This invention relates to the technical field defined above, and alternatively a radiation dose distribution on targets and risk areas or a treatment plan optimization in a large quantity of suitable problem solutions. In addition to the technical field defined above, this invention can also be used for selecting an "problem solution" consisting of multiple characteristic values from a plurality of possible problem solutions.

In conformational radiation techniques, a three-dimensional dose distribution is the goal to maximize the effect in a tumor and minimize the probability of adverse effects. The history of radiation therapy shows that greater treatment success results from introducing improved dose distributions. In the area of the torso and to some extent in the area of the head and neck, however, there are a number of target volumes which cannot get be irradiated with a high dose that conforms to the target volume because of their irregular concave shape and their direct proximity to high risk organs, even using modern techniques currently available in the clinical field such as 3D treatment planning and the use of multileaf collimators in front of a radiation head (see Bortfeld, "Dose conformation in tumor therapy with external ionizing radiation," dissertation, University of Heidelberg (1995) and Brahme, "Treatment Optimization Using Physical and Radiobiological Objective Functions," *Radiation Therapy Physics*, ed. Smith, Springer, Berlin 1995).

Due to the development of inverse therapy planning with open fields and intensity-modulated radiation therapy (IMRT), the situation has changed fundamentally in recent times. Inverse planning yields optimized dose distribution in the patient to a certain extent. In conventional therapy, field weights, wedge filter geometries and incident beam directions are determined but in IMRT intensity-modulated fields are determined. Theoretical planning comparisons and preliminary clinical experience have shown that greatly improved dose distributions can be achieved in the sense of conformation radiation therapy by using these new methods, especially in serious cases.

Inverse therapy planning uses a weighting function which assigns a single score as a quality measure to each radiation plan (see Bortfeld, Stein, Preiser, "Clinically Relevant Intensity Modulation Optimization Using Physical Criteria," *Proceedings of the XII$^{th}$ ICCR*, Salt Lake City 1997, eds. Leavitt and Starkschall, pp. 1-4 and Preiser, Bortfeld, Hartwig, Schlegel, Stein, "A New Program for Inverse Radiotherapy Planning," pp. 425-428, loc. cit.). A radiation plan in its full complexity is characterized here by a single number. A planning system then selects a radiation plan having the best score out of many plans.

In general, however, many risk structures with different relevance for the quality of life of the patient must be taken into account in such planning. Furthermore, the goal of administration of a high and homogeneously distributed dose in the target volume is in contradiction with maximum protection of risk structures. These different goals, some of them contradictory, are taken into account by defining weighting functions for each organ (i.e., for target volumes and risk structures) scaled with weighting factors and then added up. The result is the above-mentioned (single) score for the entire radiation plan.

In practice, a significant problem with this type of inverse planning is in defining the weighting factors for the relevant structures. These factors cannot be interpreted clinically, i.e., a clinical evaluation and/or arrangement of organs cannot easily be converted to a comparably arranged list of weighting factors. Therefore, the weighting is determined by trial and error, which should actually be avoided through the use of inverse planning.

This means that even in inverse planning, certain optimization steps in general are performed with different weighting factors until arriving at an acceptable plan. This is extremely time-consuming and is partially responsible for the relatively low clinical acceptance of inverse planning so far. One example from experience with inverse planning at the DKFZ in Heidelberg illustrates this state of affairs. A summary of planning times for the last 50 IMRT patients treated revealed that inverse planning took 2 to 3 hours per patient, with three to 15 plans being determined for each patient. In other words, the weighting factors were readjusted two to 14 times, with the computations being performed again and evaluated each time until arriving at a satisfactory result. However, as experience is gained in this field, group problem solutions with which adequate results can be achieved, including weighting factors and other parameters, will no doubt be found for certain standard cases. In complex cases and new cases, however, the time-consuming trial-and-error method described here will be unavoidable.

Another problem with inverse planning in its current form is the statistical nature of the planning results. The optimum solution for a fixed preselected set of weighting factors does not provide any information regarding whether, for example, an increase in dose in the target volume would be possible if higher doses were allowed in certain risk organs.

These two problems—the great amount of time consumed and the statistical nature of the problem solutions—have resulted in the "ideal plan" frequently not being found for a patient even using inverse planning methods. The main cause of these problems is the multiple criteria in the statement of problem—taking into account, i.e., considering dose distributions in target volumes and risk structures but this is transformed into a problem with a single criterion by introducing artificial weighting. This arbitrary restriction of the view to a single number also gives a physician a chance to perform dynamic changes in planning after the optimization run.

Ideally after conclusion of the optimization process, independent partial weighting functions, each belonging to the respective target volume or risk organ, should be considered and modified simultaneously in order to be able to determine a radiation plan that is optimum for the patient and to do so by a process that is both dynamic and interactive and in particular is also rapid and simple.

A preferred reference value for the evaluation of radiation effects is the biologically effective equivalent uniform dose (EUD) which is described with the help of an organ-dependent convex combination of the maximum achieved dose in the entity in question and the corresponding mean dose (max and mean model), see Thieke, Bortfeld, Kuefer, "Characterization of Dose Distributions through the Max. and Mean Dose Concept," submitted to *Acta Oncologica* (2001).

Computation of optimum dose distributions thus constitutes a multicriterial task, whereby radiation doses in different mutually independent structures (target volumes and risk volumes) are considered. The additional requirements for a high radiation in the target and the lowest possible doses in the surrounding risk organs are inherently contradictory. Therefore, the goals should be considered separately from the optimization process and the inverse radiation planning problem with a given radiation geometry should be formulated as a multicriterial optimization task. For each relevant tissue entity—whether target volume or risk organ—mutually independent goals are defined.

Thanks to EUD modeling and also with the help of the max. and mean model, the planning problem for radiation therapy can be represented in a mathematical classification as a multicriterial linear optimization problem whose target functions seek to simultaneously minimize the biologically active EUDs in the risk areas and under irradiation of the target volume.

It can be seen from the description of the state of the art that a therapy planning, i.e., a specification of radiation doses in the treatment of unwanted tissue requires an enormously complex and time-sensitive procedure with a multitude of optimization steps, different direction factors until finding a suitable plan which can still be evaluated can be evaluated differently in its optimum selection in subjective evaluation by different people treated with said plan. Each treatment time consists of a plurality of irradiations from different directions and with different doses and even with a different intensity distribution during a radiation section. Treatment is repeated after an interval of time so that the concept of therapy includes not only a single treatment but also a recurring treatment at greater intervals of time. For any treatment or therapy, controlled variables or control commands are necessary in the sense of adjustment parameters for the radiation head, the instrument and many peripheral instruments so that the (preset) therapy can take place in an automated fashion within a short period of time.

The specification of these characteristic parameters for structural objects or technical instruments should be placed in the forefront for the following solution to this problem. A solution to a problem in the case of a radiation device should be understood to include not only an overall therapy but also individual time segments of an overall therapy based on intensities and directions and composed technically of a plurality of controlled variables or commands which are based on the radiation device as a representative of operative devices in order to obtain the radiation doses in the target volume corresponding to the solution thereby found (as the target or tumor) with the desired high dose and in the risk volume (such as endangered organs in proximity to the tumor) with the lowest possible dose when subsequently implementing the therapy.

The same thing is also true of measurable or describable technical properties of a structural object included by a solution as multidimensional (multiple) descriptions.

This problem is solved with this invention according to Claims 1, 16 and 17 as well as 18 and 19 and/or 20 and also according to Claims 42 or 41.

It is assumed here that relevant (mathematically "efficient") problem solutions to the problem are calculated in advance or are predetermined and can be computed by using a known strategy and separated from the actual application. The use of high performance computers makes it possible to solve a multicriterial problem and to discover suitable settings of the radiation head, for example, and suitable intensity distributions for each of the predetermined incident beam directions in order to as a result arrive at the dose values representing the highest possible radiation dose for the target volume as the target and the lowest possible radiation dose for the one or more risk volumes in proximity to the target or in the path of the radiation to the target, each depending on the organ, even lower doses being preferred.

Technical properties of a technical object such as services, lifetime, height and weight can also be improved jointly in a "multicriterial" process.

The plurality of possible problem solutions to the problem can be stored and is represented as characteristic values for the tissue volumes (target and risk) to be taken into account in the computation through their respective effects in the sense of dose values for example. These individual doses are not combined in a scalar, not even with individual weighting factors but instead remain as a vector in the sense that each problem solution has multiple characteristic values for the individual tissue volumes.

These problem solutions presuppose that these dose values are within the organ-dependent acceptance ranges. Thus a plurality of possible problem solutions are available, one being selected on the basis of the fact that at least a plurality of the stored problem solutions, preferably all of them, delimit or form a planning zone within which an "optimum solution" (compromise solution) can be discovered by a visually simple and reproducible method.

Accompanying information may be provided with a problem solution that has been found and may change with a change within the planning area and may be represented in addition to the planning area, yielding the respective visualizations of isodoses (by layers in transverse sections) or dose-volume ratios that characterize which amount of the volume of an organ or target receives which radiation intensity in Grays (gy). These two forms of representation are customary and can make the problem solution, which consists of multiple radiation doses for risk organs and targets, found on the basis of the planning zone, visually discernible in their effect.

A more general consideration of this invention yields a much broader range of application than that of radiation therapy. This invention can prepare other planning functions with the planning zone described here and a polygon movable therein, (having been entered) as a navigation body, such as designing other technical instruments or technical objects such as engines for automobiles or for aviation designs in which the technical properties of these objects must often fulfill divergent criteria. For the engine of an automobile or another motor vehicle, the displacement, power, rotational speed and consumption may be technical parameters, but in addition, economic parameters such as image or benefit may also be taken into account. These parameters are multicriterial on the whole and have divergent development directions. For example, fuel consumption does not necessarily decrease when displacement is increased. When high costs are reduced, one cannot expect a large power range. When the stated object is an aircraft, for example, parameters such as lightweight construction, material strength, thickness of the material used in the wall area and load capabilities constitute the technical side, whereas cost, safety and lifetime are other criteria which tend to be more economically oriented but definitely have an influence on technical parameters as well. A greater expenditure for materials has a positive influence in the direction of lifetime and in the direction of safety but has a negative influence with regard to cost. Construction time can also be of influence, so that an object whose technical properties can be represented on the axis sections in the planning zone by representative values can be planned better. Additional applications are suggested in the planning of such objects as a sewage treatment facility or a refuse incineration plant where such technical criteria as space, throughput and pollution burden can be used as suitable properties (in the sense of technical parameters) whereas site determination, shipping distance and cost are economic factors but they can also have an influence on the technical factors, i.e., the technical factors alone do not determine the design and form of such a large-scale installation. This would even allow for planning of such difficult systems as the construction of a soccer stadium, where not only the site location but also other technical implementation criteria such as traffic connections, cost sharing and nature conservation regions (flora/fauna habitat regions) are taken into account in the planning or decision-making. This object can also be described by technical properties which are assigned individual axes as part of the planning zone and a line body which encloses this planning zone allows a modification of the individual technical properties for discovering one optimized solution from a multitude of problem solutions that are available.

Such technical objects which are themselves work objects, i.e., not only design objects, but also operative devices and equipment such as robots, lathes or automated assembly systems can also be described with regard to their technical properties so that optimized planning of such equipment is feasible and comprehensible. A great variety of problem solutions are therefore no longer damned to incomprehensibility but instead may form a basis for navigation on the part of the user who is then able to navigate easily among the various possible problem solutions and in doing so can easily discover the optimum values for his or her given concept horizon. From the selection thus made, the technical parameters can be taken over directly and used as the basis for further design (object design or construction of the design object) or used as the basis for further construction of operating equipment. In a special case, use of preparation of specifications which arise from the planning preparation described here is also possible.

This invention avoids the problem requiring new calculations that are widely separated in time and it is assumed that a number of advance calculations are already available, but the multitude of possible problem solutions does not overload the person performing the work and determining the result but instead presents the results to him in a plausible and visual form so that he apparently has only to compare a very small quantity of data. By varying an input navigation line body or a navigation polygon for the case when the planning zone is formed as a polygonal surface, it allows an evaluation of a polygonal form whose corner values are formed by the technical properties or by dose values for the risk areas and the targets. This polygon does not depart from the planning area and when one of the corner values is altered, the entire polygon changes within the planning area.

This is based on the fact that only one problem solution is depicted cohesively but no more than one problem solution is imparted visually to the observer in a stationary display. All the problem solutions are available for access in the database but they are not displayed as problem solutions. They are merely displayed to the observer due to the fact that on the whole the planning area represents the combination of all problem solutions that would be possible hypothetically, but the environment of the planning zone cannot be selected. The environment may be a polygonal body inside the inner edge of the planning zone plus a remaining area outside of the outer edge of the planning zone. This is possible in both 2D and 3D.

A change on one of the axes, e.g., a change on the weight axis or on the risk axis, toward a higher value, which is actually desired, changes the problem solution displayed in therapy planning so that the other dose value for the risk organs also change. In most cases it is such that not all wishes for the maximum dose for the target and minimum dose for the risk organs can be met at the same time and an optimum should be sought, but this is a highly subjective matter. Reducing radiation doses on very sensitive risk organs, for example (bone marrow or organs of sight) may result in other risk organs receiving higher radiation doses and the target also receiving a higher radiation dose—which is actually desirable. Other risk organs may be less sensitive, e.g., the lungs, so that a higher radiation dose does not do as much damage there as it would to more sensitive organs.

The user is completely free to make subjective choices; a visual change in the line body input allows qualification of the problem solution displayed as more or less suitable at a glance.

It should be emphasized that multiple problem solutions cannot be linked together in the display but instead only one solution is selected on the basis of the cohesive navigation line body as a polygonal structure that has been entered and whose points of intersection with the axes represent the characteristic values of the radiation dose of the vector described above or the score vector or radiation dose vector of a problem solution.

The same thing is also true of the technical properties of other equipment or technical objects (entities influenced by design).

A change to displaying another problem solution can preferably take place in a fluid manner following a transition state in which the one problem solution is faded into the other solution within the planning zone (Claim 8). The quality of a change can be evaluated here by the change in the navigation body input, which as such preferably does not have any jumps.

Each of the several axes forms a radiation dose scale for a tissue volume, for example, such as the target volume and the at least one risk volume, preferably two or more risk volumes. These axes are applied in a visual form to a display device such as a display screen and are referred to below as the risk axes and the target axis. No two axes coincide and all axes arranged side-by-side form an angle greater than zero between them. Adjacent axes do not run parallel in order to be able to span at least one area (2D consideration).

Characteristic values are shown on each axis and the total number of problem solutions stored defines a particular axis section on each axis. This axis section is an acceptable interval which has an upper end and a lower end predetermined by the problem solutions and their characteristic values of radiation doses based on the particular risk axis or target axis affected.

The acceptance intervals define the planning zone when their particular upper limits and lower limits are interconnected. To illustrate the planning zone with respect to the environment, this is depicted differently from the environment.

This offers the user of the planning tool as a system or method or visual representation (Claims 17, 18, 43, 44) the possibility of discovering within the planning zone a navigation polygon or the line body described above which is most suitable for him personally for a subsequent therapy or an entity that is influenced by design. An enormous volume of possible problem solutions is thus easily made available, with an even greater number of technical parameters behind them for the settings of the technical equipment, in particular radiation therapy equipment being investigated in the sense of a property distribution or a dose distribution in the organs and risk areas whereby the actual therapy is not yet taking place but instead is merely being planned, said planning being (far) before the actual treatment takes place and thus it does not take place directly concurrently with this therapy (Claim 10).

Certain characteristic values on the risk axes and the target axis can be defined or fixed in order to be able to be concerned mainly with the change in the remaining characteristic values on the other axes (Claim 12). To simplify this change and for a visual representation of the restriction on the problem solutions that are now possible, a (two-dimensional) section of the planning zone can be considered separately. This is done by separating it visually so that it is shown as lighter than the remaining planning zone, for example, or in a different color. All the problem solutions which have an inferior characteristic value as the dose which is on the axis on which the characteristic value has been fixed are then locked out (Claim 12).

This also results in reductions or eliminations in the remaining planning zone in which the locked out problem solutions extend due to the connection of the points on the risk axes and on the target axis.

Multiple axes may be fixed with the respective characteristic dose values so that multiple sections can also be selected from the total planning zone.

The individual sections selected out of further planning (and the planning zone) may also be added again (Claim 13).

In the case of a (planar) polygon, this blockage is to be equated with a fixation of the crown point and all characteristic values between the crown point and the exterior edge line, i.e., the bordering polygon on the outside are blocked.

The problem solutions stored in the database may preferably be pareto-optimal problem solutions. It is time-consuming and pointless to depict all possible problem solutions. However, it is appropriate to calculate a suitable representative system from the quantity of (mathematically) efficient problem solutions. In practical implementation, such a representative system usually consists of 100 to 200 or more problem solutions which are stored in the data base and can be made available visually. A rapid selection from the multitude of proposals in the database is possible despite its extent and can be set up for a patient individually or planned for him in advance to take into account in accordance with the course of his or her disease and the personal subjective perception on the part of the operator making the decision.

The same thing is also true of planning the technical properties of a design object.

The pareto-optimality is based on the assumption that the multicriterial optimization problem is to be solved in such a way that the target function for radiation therapy seeks to minimize a predetermined (biologically active) EUD (equivalent uniform dose) in the risk areas and at the same time to minimize underirradiation of the target volume (the target), whereby not all the predetermined values (the upper limit values as desired values for the target and the lower limit values as desired values for the risk area) can be met at the same time, but approximately optimized problem solutions can be found in an overall view in the case of pareto-optimality.

A plurality of these problem solutions then advantageously form the content of the database described above which is individualized via the planning to only one problem solution which is to be applied subsequently.

The general applicability of the technical concept of the planning tool described above is illustrated by the independent claims (Claims 40, 41), which can also be regarded as a planning diagram (displayed on a display screen) or as a method of displaying such a diagram. Likewise as in the possible therapeutic uses of the results found here, it is not the planning itself that is the object of the claim but instead making possible such planning by providing a suitable tool with which this planning can be implemented.

Exemplary embodiments illustrate and supplement the invention.

The application contains at least one drawing executed in color. Copies of this patent or patent application publication with color drawing(s) will be provided by the Office upon request and payment of the necessary fee.

FIG. 1 shows a schematic diagram of a technical device, here in the form of radiation device 10, 11 having an axis 100 about which the moveable part of the instrument with the radiation head 12 can be pivoted, with the pivot angle α being adjustable. This also shows the memory unit 5 having a main memory 1 which contains a database.

FIG. 2 shows a schematic view of a transverse section of a patient having three wrist organs $h_1$, $h_2$ (lungs) and $h_3$ (spinal cord) and a target organ T as a tumor.

FIG. 2a through

FIG. 2e show symbolically intensity distributions such as those obtained by a multileaf structure in front of the radiation head 12 from FIG. 1. The figures are arranged with respect to FIG. 2 so that a particular intensity distribution at the pivot angle α shown in FIG. 2 is used according to FIG. 1 as in FIG. 2a with the intensity distribution shown there from the angle $\alpha_1$, FIG. 2b from the angle $\alpha_2$, etc.

FIG. 3 illustrates schematically the multileaf settings of strip-shaped leaves 13, 14 which leave an interspace 12a of the head 12 as clearance through which radiation whose intensity is distributed over a certain geometry or contour exits.

Figure 5:
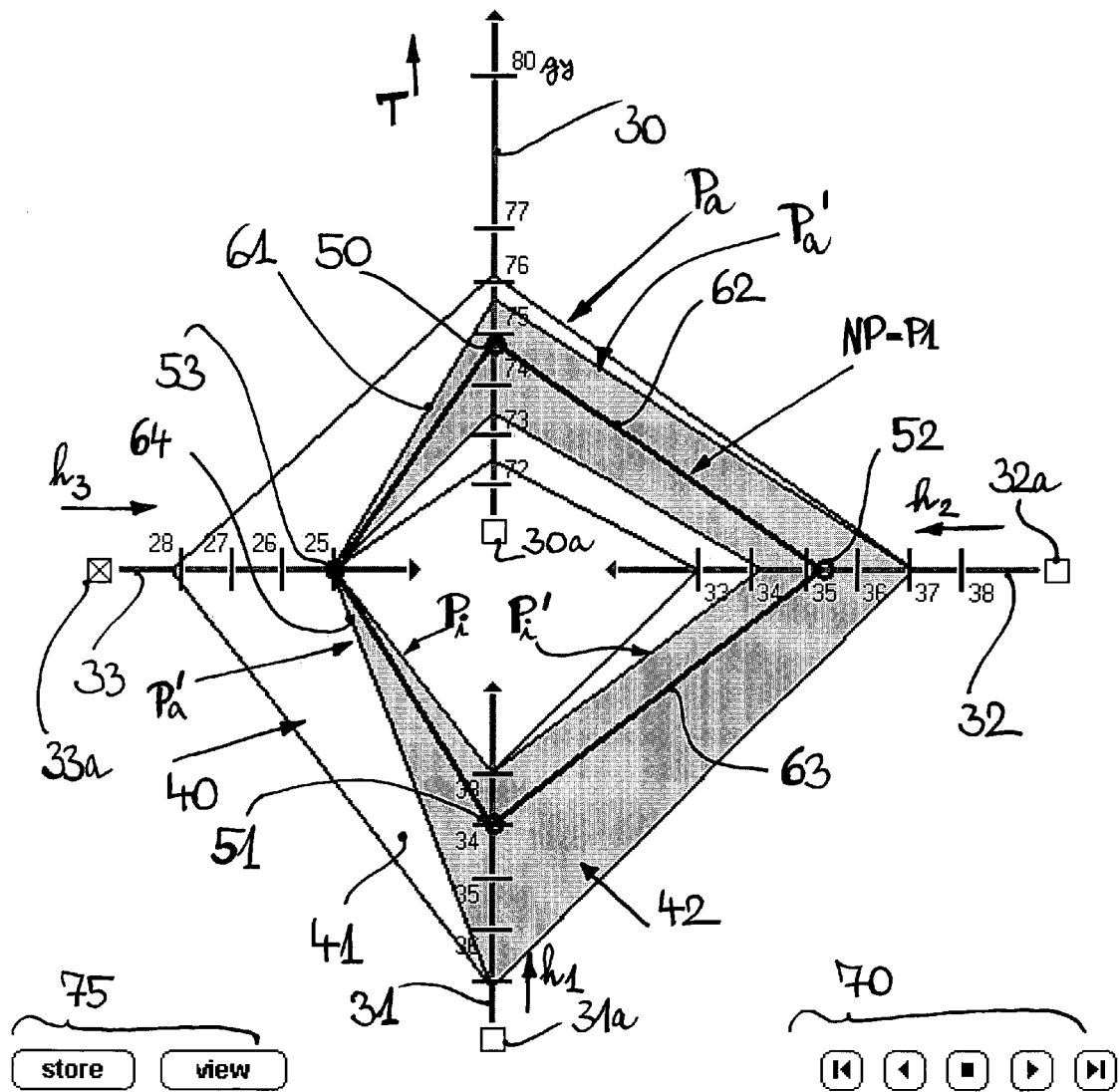
FIG. 5 illustrates a two-dimensional representation of a planning zone 40 with all the graphic components used therein for predetermining control values or controlled variables such as the controlled variables for setting the multileaf structure in FIG. 3.
Figure 6:
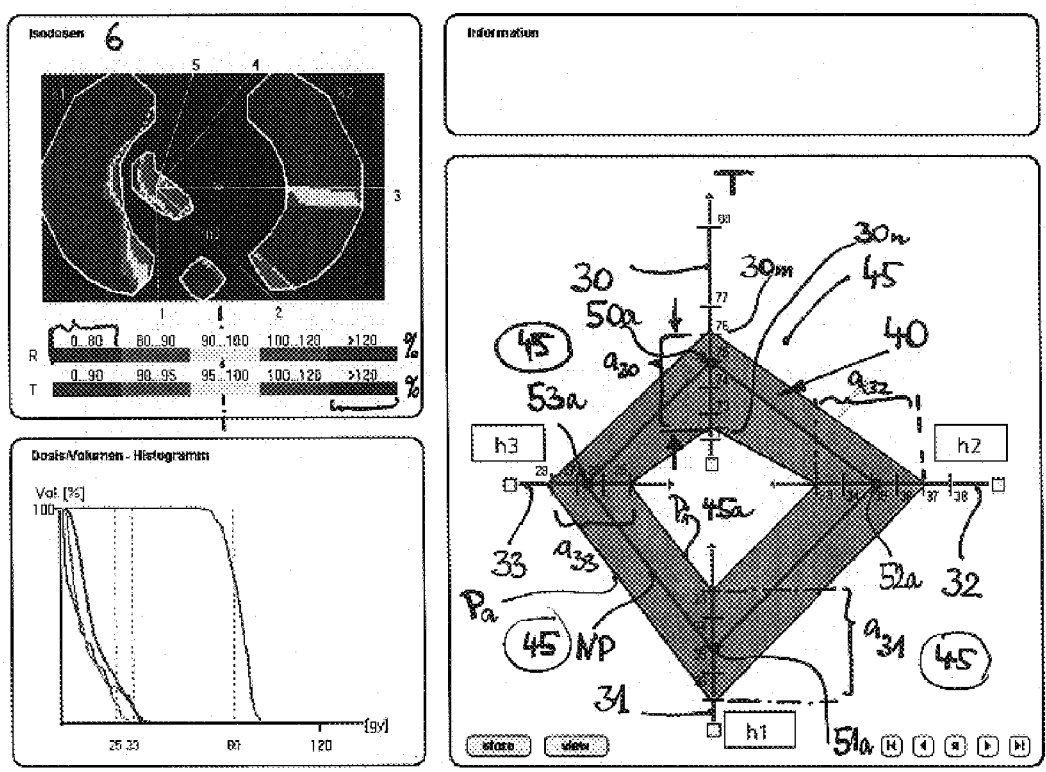

FIG. 6 shows a (colored) survey of all the graphic structures which are used in the following figures in an example of planning a therapy which can later become the object of the treatment after their off-line determination. This illustrates the start of a planning session in which the planning surface 40 is occupied by a few additional elements to illustrate their function and to relieve the reference notation in FIG. 5.

Figure 7:
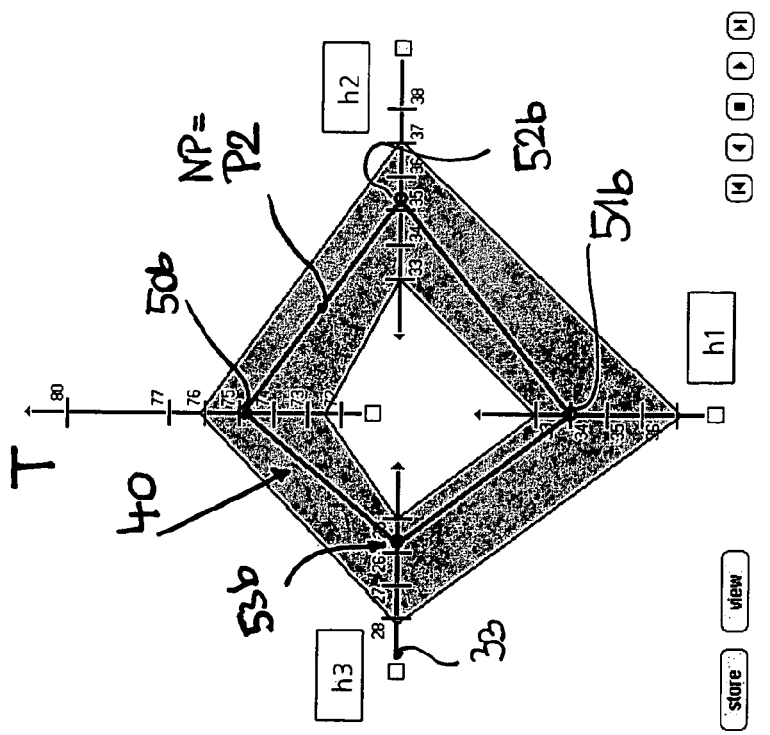

FIG. 7 shows the planning surface 40 from FIG. 6 with a modified polygon P2 as the navigation polygon or navigation line body within the planning surface 40 which is depicted here in 2D.

Figure 8:
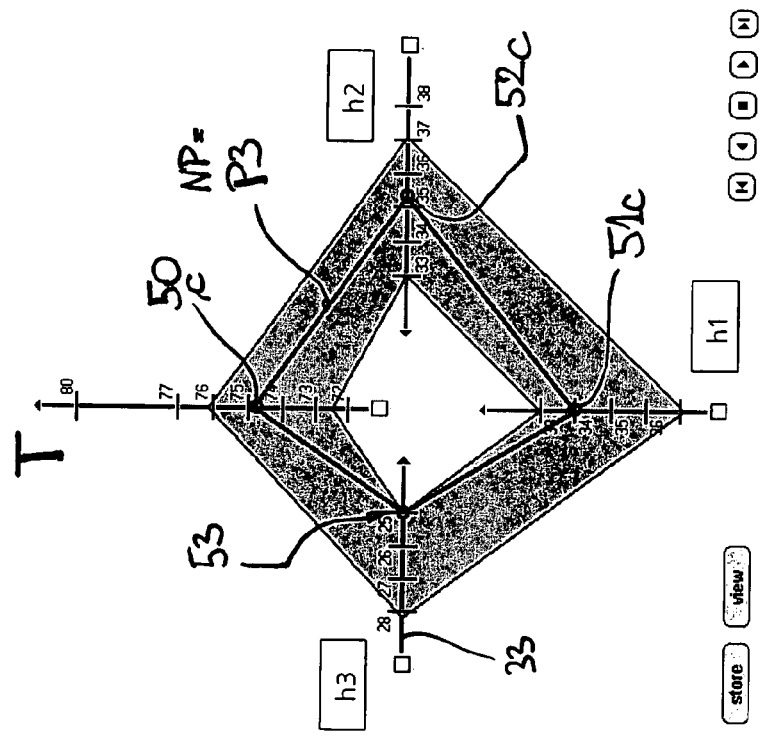

FIG. 8 shows another step with a further reduced dose in comparison with FIG. 7 with regard to the risk axis $h_3$ to 25 gy.

Figure 9:
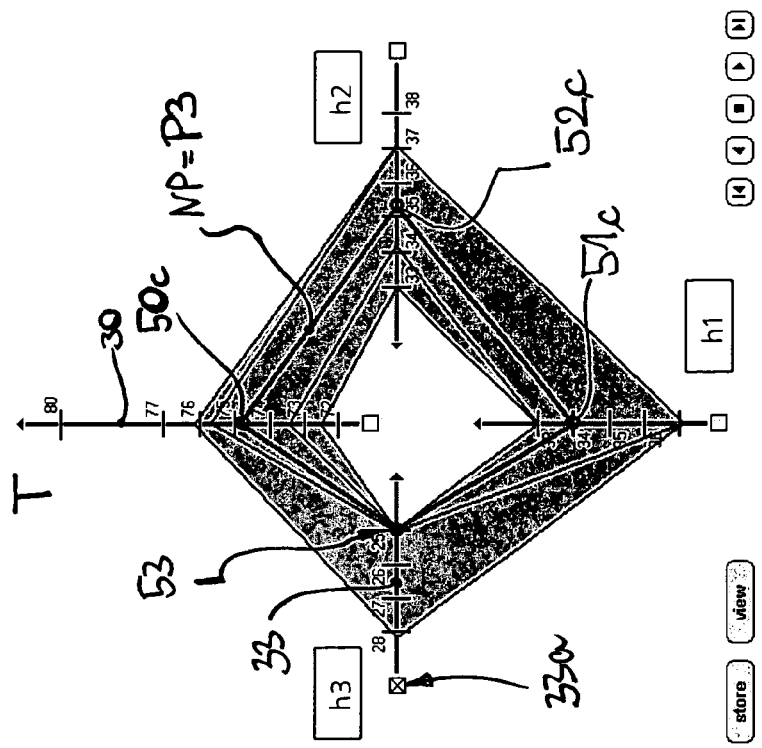

FIG. 9 shows a plot or determination of the aforementioned value of 25 gy on the $h_3$ axis and masking out at least the left section above the characteristic value 53.

Figure 10:
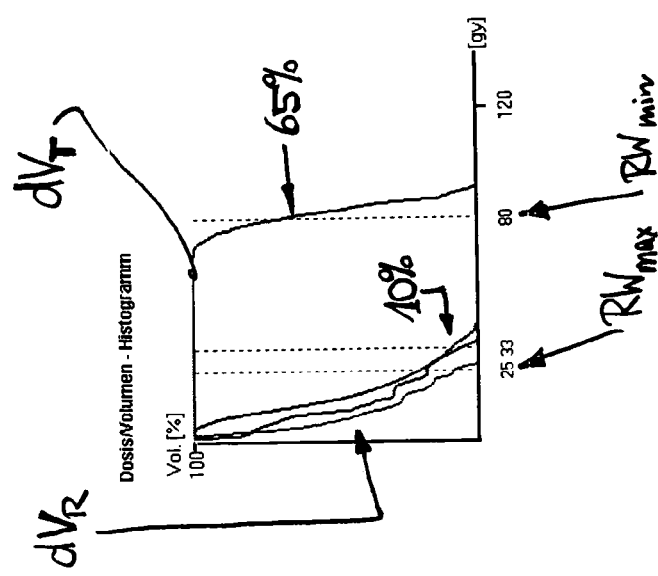

FIG. 10 shows a change in the upper characteristic value 50c from FIG. 9 to the value 50 with 75 gy on the target axis T.

FIG. 11 shows a diagram of a volume histogram as a 3D representation on a two-dimensional diagram.

Figure 1:
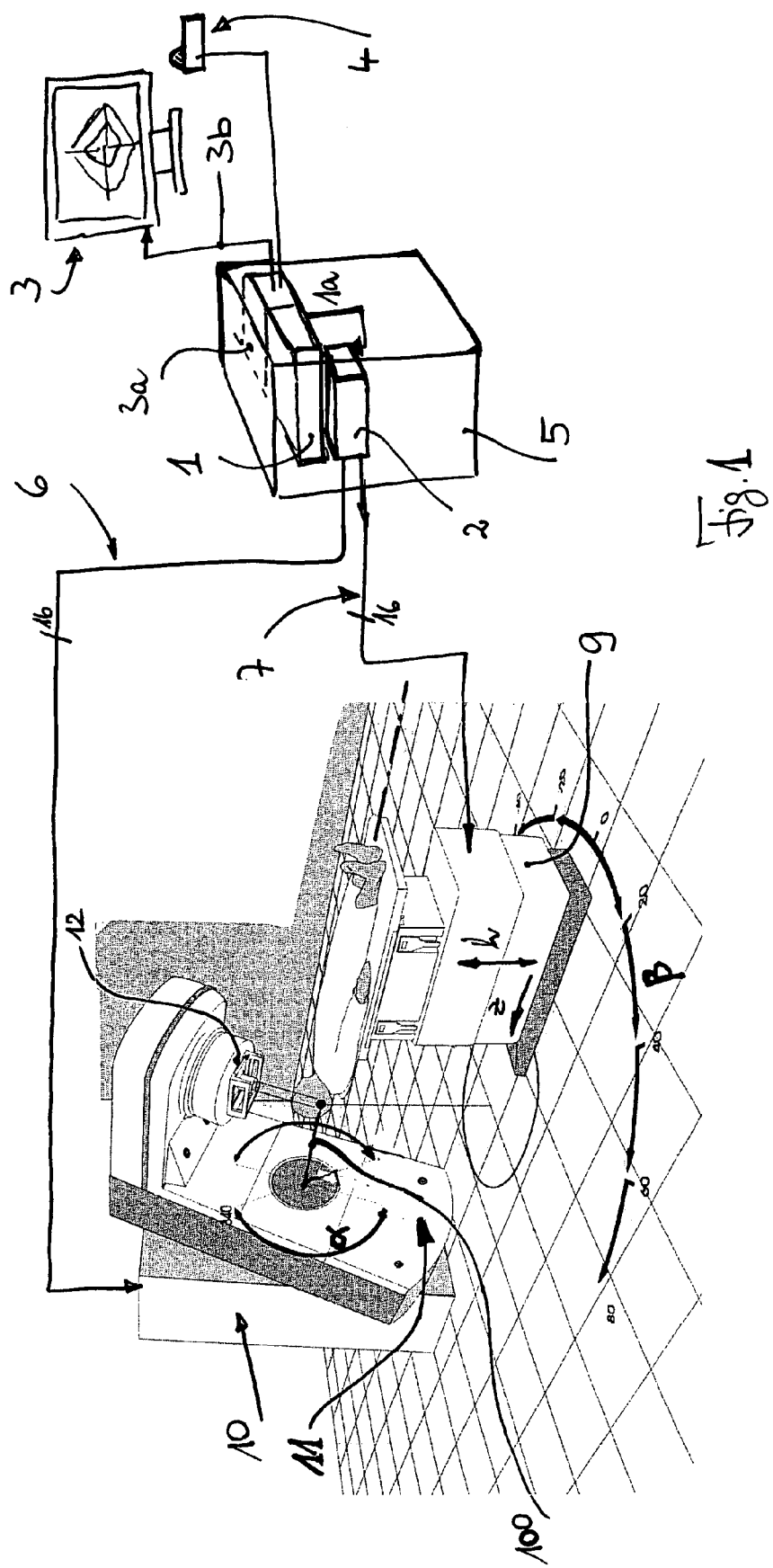

The planning for a therapy which is selected here as an example and is not directly related to the planning but instead proceeds at a different time and place is illustrated in the survey diagram in FIG. 1. A display screen 3 presents graphic illustrations of problem solutions which are offered to a user or an operator, usually a trained physician, and which provide him or her with a possibility of visual representation. This shows problem solutions that are calculated in advance and are stored in a memory in a database 1 in the control system 5. These database problem solutions are transferred via a graphic interface 3a to the display screen 3 over the control line 3b. A control device 4 for influencing and executing interactive entries is placed close to the display screen 3 within the range of the user.

Once a problem solution has been found in the database—with the problem solution being a compilation of a plurality of controlled variables of a radiation therapy device, for example—it is transmitted via the control line 1a to another interface 2 as part of the control system 5, where it can be stored temporarily. It can then be relayed digitally to another control and monitoring device 10 of the radiation therapy device via control lines 6. It can also be transmitted via another data line 7 to a supporting device 9, which can be lifted or rotated. The supporting device 9 for supporting a patient can be rotated at an angle β (beta) and can be moved in height h and in the longitudinal direction z. The radiation therapy device consists of a fixed system part 10 and a second part 11 which is pivotable about the axis 100 and carries a radiation head 12 which is directed at a patient who is hypothetically on the supporting table 9. With the movements described here, the radiation head can be adjusted in several directions α, to which end corresponding controlled variables are relayed to it. A radiation dose of the radiation head 12 is explained with the multileaf collimator according to FIG. 3 as described in greater detail below. In addition to rotation about the axis α, rotation about the axis β and shifting the height of the table as well as the position of the table are performed with control by the controlled variables or control commands which are taken over as setpoint values from the database 1 of the control unit.

If all the characteristic values for one treatment session have been transmitted and set in the instrument, the treatment can begin but that is not the object of the present patent.

The problem solutions stored in the database are pareto-optimal problem solutions in this example, which constitute a diminution of an optimum solution in order to be able to find any problem solutions at all that are acceptable given the contradictory goals in a multi-criteria system.

A pareto-optimal solution is a compromise between under-irradiation and over-irradiation, taking into account whether it is a risk organ or the target organ. In the former case, maximum values must not be exceeded and in the latter case the values should not go below the minimum values and at best maximum predetermined setpoint values should be obtained without causing a burden on the risk organs that goes beyond the limits established.

Three risk organs are assumed below with a target volume T as illustrated in a transverse section in FIG. 2. It should be emphasized again that it is not a therapeutic process that is described and claimed here, but instead this invention pertains to the particular combination of the method described here to permit a therapeutic procedure, this combination being illustrated by the fact that the results obtained are presented in a functional technical context, which should be achieved with a brief description of the therapeutic procedure as well as a detailed description of the preliminary work.

To do so, FIG. 2 shows schematically the transverse section at the level of the patient's kidneys, for example, showing two lungs $h_1$, $h_2$ as two risk organs and a spinal cord $h_3$ as a risk organ which is at increased risk. A tumor T is imaged as the target object and is in this case situated between the lungs, approximately at the level of the liver. In this regard five directions $\alpha_1$, $\alpha_2$, $\alpha_3$, $\alpha_4$ and $\alpha_5$ are shown, representing five directions from which incident radiation may be administered with the head 12 with an appropriate adjustment of the pivotable part 11 so the adjustable angles α from FIG. 1 can correspond to the angles $\alpha_1$ through $\alpha_5$ in FIG. 2. A corresponding displacement of the supporting device 9 in direction z is also possible, optionally by also pivoting the table by the angle β in order to reach the position with the radiation head 12 as shown in the sectional view in FIG. 2.

The effect of a head 12 modulated in its radiation intensity with any desired radiation such as photons, electrons, heavy ions or protons is illustrated by the schematic diagrams in FIGS. 2a through 2e. FIG. 3 should be used for this purpose, showing a head structure 12 provided with multiple strips, where the effective head window 12a is adjusted within a frame 12b of laterally displaceable strip structures 13, 14. Both the geometry and the position of FIG. 12a are variable when the corresponding longitudinal movements or longitudinal positions are considered as control parameters. This longitudinal position $x_1$ through $x_3$ and $y_7$ and $y_8$ as the respective representatives of the strips 13 and 14 are controlled variables which are to be adjusted and yield intensity distributions in the grid structure such as those illustrated by FIGS. 2a through 2e. If radiation is emitted again with control leaves 13, 14 adjusted differently, intensity distributions with different intensities within the frame of the grid can also be obtained. The window between the intensity-modulated grid fields, shown as black in FIGS. 2a through 2e, is to be seen according to the window 12a in FIG. 3.

FIG. 3a illustrates again and emphasizes schematically the adjustment of different angles $\alpha_1$ through $\alpha_3$ with intensity-modulated radiation fields such as those obtained from a combination of FIGS. 1 and 2.

Figure 3A:
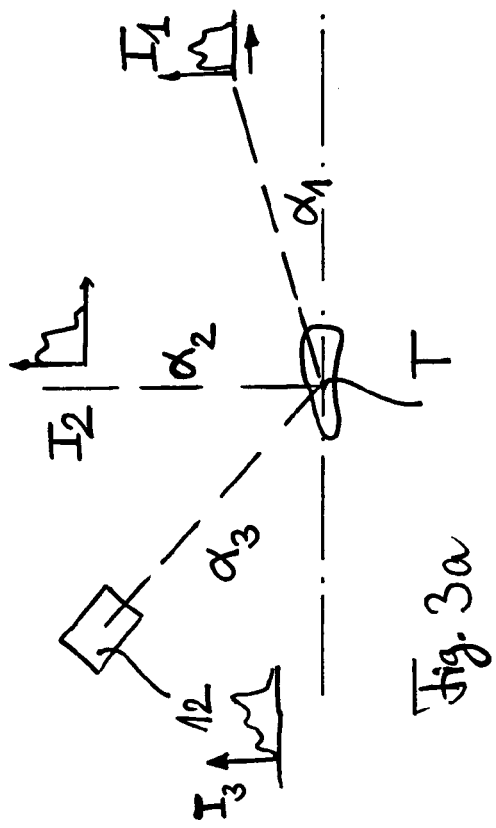
FIG. 3a illustrates different incident beam directions α with radiation influences whose intensity is modulated from a particular direction based on the target T.
Figure 3:
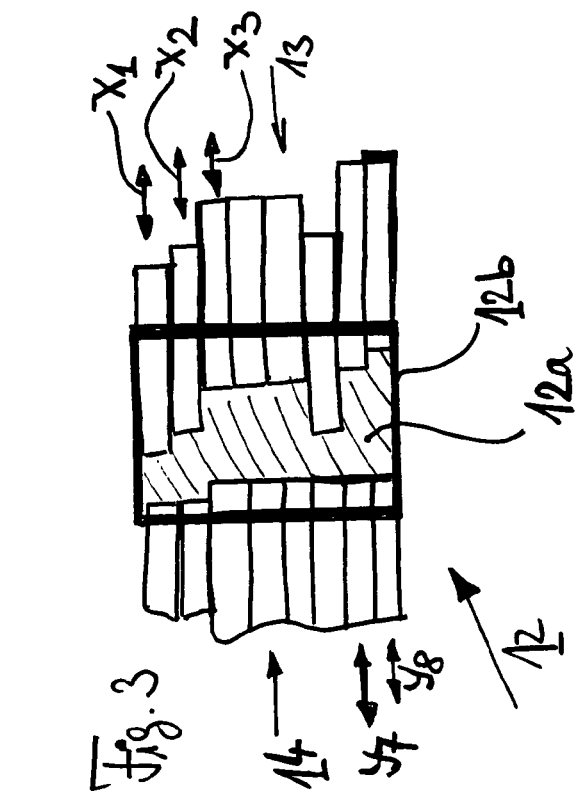

FIG. 3a illustrates the target T as shown in FIG. 2. The different target directions $\alpha_1$, $\alpha_2$ and $\alpha_3$ are shown and from a respective target direction a predetermined radiation profile with an intensity distribution $I_1$, $I_2$ and $I_3$ can be seen pertaining to head 12 which was explained above in conjunction with FIG. 3 and FIG. 1. The target which is receive a very high radiation dose (known as a curative dose) as the target volume in order to achieve a high probability of control of the clonogenic cells corresponds to that in FIG. 2 but it is not being claimed here in the discussion and instead its importance and effects after use of the results of the search for problem solutions described here are to be illustrated.

Figure 4:
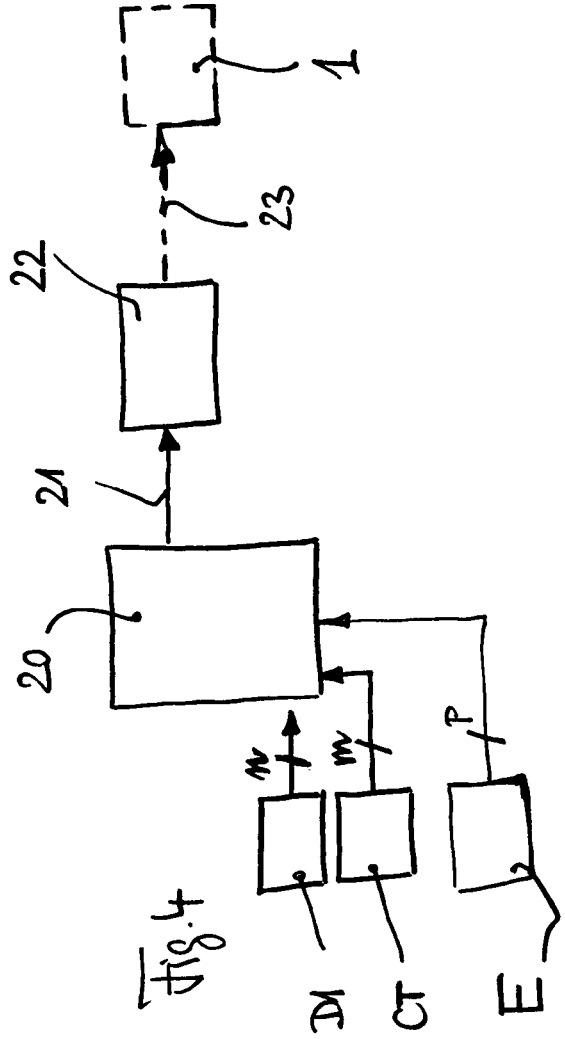
FIG. 4 shows a block diagram of the computer configuration 20 for computation of problem solutions for the database 1.

FIG. 4 shows a schematic representation of the data reproduction and the data flow such as that discernible in the right half of FIG. 1. A memory bank or a database 1 corresponds to that in FIG. 1. It receives all the calculated "problem solutions," which include the following parameters, from an interface 22 over a data path 23:

A number of radiation directions in the sense of $\alpha_1$ through $\alpha_n$ as illustrated in FIG. 3a.

A specification of radiation doses which are predetermined as the grid segments according to the FIGS. 2a through 2e for a collimator or a radiation head 12 and are to be adjusted there with regard to the surface design of the grid and also with regard to a particular respective irradiation time in order to be able to adjust intensity distributions, not only with regard to the shapes and form corresponding to the adjustment of the grid lamina or leaves according to FIG. 3. If multi-data records are submitted per radiation direction $\alpha_1$, this corresponds to multiple superimposing of different raster images or area grids which are superimposed successively at the same angle α and thus yield on the whole an intensity distribution curve like that shown in FIGS. 2a through 2e. The structural appearance of the radiation head may also be regarded as a "radiation pattern" per direction, with each raster of the pattern being represented by a gray value in such a way that a certain radiation dose between a minimum value and a maximum value is achieved here at the spot or raster element.

Data regarding the definition of the location of the organs and their three-dimensional extent can be transmitted via the data interface 22, e.g., separately from the actual problem solutions, for a visual display from the database 1.

A computer system 20 according to FIG. 4 calculates the controlled variables described previously with them being presupposed in time, using input variables D1 and CT for this purpose. The results obtained in the calculation are the "problem solutions" in the sense described above which are relayed over the data line 21 to the unit 22 which was also described above.

The starting points for the advance calculation of problem solutions with "score vectors" in the sense of radiation dose for the individual organs and risk areas are calculations of pareto-optimal problem solutions by the computer system 20 with specification of at least the following values:

Specification of a starting problem solution E based on angle settings α and collimator settings of the head 12 from which a calculation of the multiple pareto-optimal problem solutions is performed starting on this basis, with the results being relayed over the data line 21 to the unit 22.

Limit values are specified, these values being defined for each organ and being both minimum values for target organs and maximum values for risk organs. These limits may also be upper and lower limits but they may also be minimum values and maximum values. These boundary conditions are referred to in general as D1, referring to values that are sent to the computer unit 20.

Likewise, a definition of the position of the organs $h_1$, $h_2$, $h_3$ and the target volume T is sent to the computer unit 20 by specifying CT diagrams or cuts to define their relative position and their spatial extent.

It may also be specified, if it is not calculated separately by the unit 20, to indicate which angular positions $α_i$ are to be used as the beam directions. These variables fall under the specified values D1.

For example a previously known treatment plan for a certain patient having a tumor that has already been diagnosed may be used as the starting problem solutions E of the dimension p at the beginning of the calculation of the pareto-optimal problem solutions in computer unit 20. An empirical problem solution may also be used as the starting point, as can a standard problem solution. Starting with this, taking into account the boundary condition D1 of the dimension n and the physiological parameters through computer tomography CT of the dimension m, the pareto-optimal problem solutions are calculated, these problem solutions having been fed into the database 1 via the data line 21 and the unit 22 over the data line 23 after completing the advance calculations, leading to the visual display that is described below.

Although any number of target volumes may be used, the description will be based on a target volume T as the target. Although the operation will also function with (just) one risk volume $h_3$ in addition to the target volume T, this example will be illustrated on the basis of three risk volumes in the sense of three organs $h_1$, $h_2$ and $h_3$. Another way of saying this is that at least two volumes are to be irradiated, one of them receiving a much higher radiation dose than the other. If there are multiple risk organs, then multiple risk volumes are to be exposed to a low radiation burden and one target volume is to be exposed to a considerably higher radiation burden.

Examples include approximately 33 Gray (gy) for a lung, slightly higher for tissue without an organ structure, and for organs at greater risk such as the spinal cord at 25 gy or less than 10 gy for optic nerves. These limit values enter the computation by computer 20 through the parameters D1; the computer performs computations with volume elements (voxel) and determines the total burden on an organ or the target on the basis of the burden for the individual volume elements, which can be compared with a calculation over finite (spatial) elements.

FIG. 5 illustrates a planning zone 40, which consists of two sections 41 and 42. FIG. 5 is a display on the screen 3 described above, this display being obtained in an advance stage of a planning session; this display will first be described with the graphic elements used in it before reference can be made to a working session which can begin with FIG. 6.

This does not show controlled variables but instead depicts a "problem solution" of a radiation therapy plan which itself includes a plurality of said controlled variables and control commands, as already mentioned above for the radiation therapy device. This information which is stored in database 1 is not depicted but instead the score vector is depicted in the sense that characteristic values of radiation doses for a target volume T and for at least one risk volume, in this case three risk volumes $h_1$, $h_2$, $h_3$, are used to define the planning zone. The planning zone 40 graphically outlines the plurality of technical controlled variables that stand behind each problem solution and does so with the characteristic values which correspond to the radiation doses, said problem solution consisting in the example presented here of four radiation doses 50, 51, 52 and 53 which are assigned to the three risk organs $h_2$, $h_1$, $h_3$ and to the target T for this solution.

In the case presented here, a linear connection of the four characteristic values described yields a two-dimensional polygon NP, which forms as a navigation line body a quadrilateral within which the planning zone which is depicted here as an area and is bordered on the inside and outside by interior and exterior polygons $P_i$ and $P_a$ respectively. The navigation polygon NP=P1 is inside this region. This region may also be three-dimensional and it need not necessarily have a polygonal structure but in the case described here this structure is advantageous with regard to its easy traceability, with a complex multitude of problem solutions standing behind it.

In the example described here, the navigation polygon NP is defined by the four points 50 through 53. Each point is located on one of the axes 30, 31, 32, 33, with the risk axis 30 pertaining to the target T being between doses of approximately 72 gy to 80 gy. The two risk axes extend over lower radiation doses between 25 gy and 28 gy for $h_3$ and 33 to 37 gy for $h_2$ and $h_1$ each. The axes shown here are such that no two axis are identical and adjacent axes, e.g., 32 and 31 or axes 30 and 33 do not coincide, so that the planning zone 40 can span the distance between the interior polygon $P_i$ and the exterior polygon $P_a$.

Within this navigation zone, the characteristic value 50 for the target on the axis 30 to the characteristic value 52 for the risk organ $h_2$ are connected by a straight line as the distance 62. The connection to the other points 51 and 53 is accomplished accordingly, each being connected to the adjacent axis and the characteristic quantity given there for the radiation dose of the solution being depicted at the time. Thus as an example the connecting distance 63 between the radiation doses 52 and 51 is represented on the two risk axes $h_2$ and $h_1$. The other connecting distances are derived from the relationship and are not labeled separately.

Only section is shown for the radiation axes each of which contains a scale; this section includes at least the section in which characteristic values for radiation doses from the stored problem solutions of database 1 are located. All the problem solutions taken together or at least a significant portion of the available problem solutions generated previously by a computer 20 according to FIG. 4 form the navigation zone 40 as a navigation space which is described below so that the external border is $P_a$.

It should be pointed out here that this external line need not constitute a solution but instead is composed of points which originate from different problem solutions. A solution is merely represented by the fact that an internal navigation polygon NP, represented here as P1 for one solution, is depicted visually. The visual representation is accomplished with a discernible contrast in comparison with the color or the gray value of the navigation zone which is in turn shown that it is differentiated in color or in terms of the gray value or otherwise perceptibly differentiated from the exterior space which is not in question or the interior space which is also not in question.

The two regions of the visual display which are considered together as the surrounding area are characterized as 45 and 45a in FIG. 6. FIG. 6 shows a precursor stage to that in FIG. 5 but where there has not yet been a change in the characteristic value 53a in comparison with the interior limit value 25 gy on the axis 33.

It can be seen here that the respective interval $a_{30}$, $a_{31}$ has been formed no the axes 30 and 31 respectively from characteristic values of problem solutions which are available in database 1. The same thing is also true accordingly for the axes 32 and 33 and the intervals $a_{32}$, $a_{33}$. These intervals or sections of the axes 30 to 31 which are referred to as acceptance intervals form the specifications for the navigation zone 40 which is plotted as an area and is depicted as being gray in comparison with the environment 45, 45a.

The navigation polygon NP here is shown as a polygon within the zone and is emphasized in comparison with it. Only one solution is depicted here which can be referred to as the starting solution; starting from this solution a user can make a change in the solution depicted within the context of the following FIG. 7ff.

To do so here one should start with the characteristic values 53a shown according to FIG. 6 on the scale $h_3$, 51a on the scale $h_1$ and 52a on the scale $h_2$ corresponding to the axes 33, 31 and 32. These three risk axes are arranged at an angle of 90° each. A target axis 30 is show pointed perpendicularly upward, its dose value shown as characteristic value 50a.

To rephrase technically, this solution means that a radiation dose of 75 gy has been allocated to the target for the case of selection of this solution, while the risk organs will receive the radiation doses indicated by them accordingly. An upper limit value of 30m on the target axis would be desirable corresponding to 76 gy and a lower (internal) limit value on the other risk axes, although these cannot both be achieved together in one solution according to the pareto-optimal problem solutions for the stored quantity of available problem solutions described previously. The desired radiation value of 80 gy on the target axis has also been eliminated because this could not be retained within the problem solutions calculated in advance without violating the other boundary conditions of the risk axes.

The upper and lower limit values 30m and 30n are target axis 30 should also be explained where corresponding upper and lower limit values can also be found on the risk axes 31, 32 and 33. With these limit values, the acceptance interval is limited on each axis so that all characteristic values of radiation doses come to life within or at least on the edge line of the planning zone 40. From the starting illustration of FIG. 6, a new solution is sought whereby the radiation burden for the risk organ $h_3$ is decreased—as requested by the user and as assumed here for the purpose of illustration—so the value 53a is to be shifted toward lower radiation values. At the same time the radiation dose 50a for the target is to be increased. The two radiation doses are to be improved, one is to be reduced and the other is to be increased.

All the available and possible problem solutions are present in database 1 and were stored there in advance. They are selected out individually in the course of the following FIG. 7ff by modifying one of the corner points of the polygon NP of FIG. 6 in each case.

However, before describing the way to leave FIG. 6, the diagram in the left area of FIG. 6 is to be explained further as already illustrated in FIG. 2. With regard to the second representation on the left side (the lower diagram) reference is made to FIG. 11 which is to be explained later. In the case of the navigation polygon which is shown visually as a possible line body representing one solution of the stored problem solutions of database 1, this yields a radiation burden according to the transverse section through the upper left detail figure from FIG. 6. This corresponds to FIG. 2. The five directions $\alpha_1$ through $\alpha_5$ can be seen as well as the volumes corresponding to the axes 30 through 33 at one of many possible axial heights. On this transverse plane, this also yields the local radiation burdens represented as $h_{22}$, $h_{21}1$, $h_{11}$ through different gray values in FIG. 2, with a scale at the lower edge to indicate whether deviations in the upper or lower direction would be achieved for the risk organ in the volume element zones and whether deviations in the upper or lower direction would be achieved for the target area if the solution depicted in the polygon were to be selected and used for a subsequent therapy.

These different radiation doses on the transverse plane may be characterized with colors, whereby deviations in the lower direction can be obtained in the case of risk area R and deviations in the upper direction can be obtained in the case of target T with the same colors. Therefore the particular target direction is depicted with the same color while the other deviations are depicted with another color but can also be characterized with the same color. Reference is made to the color display of FIG. 6 for explanation. A glance at the transverse section shows the observer the physical effect of the polygon NP which has been selected and is to be handled as such abstractly and separately from the physics but is easy to handle. A change in the axial height in the direction 100 in FIG. 1 corresponds to a different transverse section and would yield a different distribution of the radiation doses with no change in the navigation polygon NP.

The assignments of 0 to 80% with regard to the risk areas $h_1$, $h_2$ and $h_3$ are characterized with the same color as the target above 120% on the accompanying FIG. 6, which is in color. In the target T according to the graphic representation the predominant portion is between 95% and 120% while most of the volume portion in the case of the risk areas is in the range below 80%. The colored characterization of the radiation value to be improved for the risk $h_3$ as depicted here corresponds to shifting the point 53a toward the interior in the direction of the (green) arrow depicted there which indicates an improvement. Corresponding arrows can also be provided in the other risk axes, while an arrow in the opposite direction pointing toward the target axis T indicates the target direction for an improvement there.

The planning session and the planning tool work in the direction of reducing the dose of $h_3$ and increasing the dose of T in the case of the improvement on FIG. 6 so that for example the corner point 53a can be shifted by the user so it is discernible and sensitive on the image representation that with the help of a control tool such as a mouse or a pad 4, this spot can be picked up and shifted in any direction desired so that for example it comes to rest at 53b at a radiation value of 25.5 gy with the planning zone 40 unchanged and also with no change in the scaling of the axes 30 to 33.

This corresponds to a direction to another solution to be displayed although it need not necessarily have a corner point at the point 53b as shifted by the user. The planning tool, i.e., the hardware or software standing behind it in the control unit 5 allows a point for this which is closest to the point to which the user has shifted the point 53a on the axis 33. To this end, sorting according to the $h_3$ value and selection of the most proximate point are suggested for a database. On the basis of the predetermined direction, this corresponds to a narrowing of the beginning of a new navigation polygon which is to be formed and is depicted here as already having been formed as p2 in FIG. 7. The solution depicted here consisting of points 53b, 50b 52b and 51b corresponding to the score vector with the characteristic values for the radiation doses for the individual axes corresponds to a previously stored solution required by the user with regard to the value 53b.

The other points 50b, 52b and 51b are determined according to a search structure so that all these three other points are as close as possible to the previously valid radiation values on the same axes, namely in this case the values 50a, 52a and 51a in FIG. 6, but all of them belong jointly to one solution which has the radiation value 53b (or comes closest to that). The search control is thus able to modify the navigation polygon slightly so that it can undergo a great change on the axis on which the user is making the change while on the other axes it undergoes only the changes that are still available with regard to the variety of possible problem solutions predetermined by the point 53b. Corresponding database search structures allow (through sorting criteria and selection) the computation of a minimum deviation in the sum of the individual deviations at the points 51a, 52a and 50a in comparison with the solution presented at the time and thus permit a selection of a single solution as a novel navigation polygon P2 to be displayed. Other search criteria and changes for the other points which are not being actively shifted are also possible—only one of several possibilities is explained in greater detail here.

It is also possible to modify one of the other characteristic values 50a, 52a and 51a from FIG. 6 so that then the corresponding other particular three values are shifted, taking into account the representation of just one solution which is at least similar to what has been presented before.

With regard to the change in sequence in the side-by-side displays of the isodoses and the dose/volume histogram, a corresponding display like that in FIG. 7 is also provided so that it is possible to show visually which radiation burdens change in which transverse sections due to a change in the position, areas and size of the individual color assignments as explained with reference to FIG. 6.

It is then also desirable based on FIG. 7 to further improve the dose on the axis 33 to $h_3$, i.e., to reduce the dose in the direction of the arrow shown here. With this change toward FIG. 8, it should be assumed that the user has shifted point 53b to the inside end toward minimum dose 25 gy and has influenced the control tool 4 there (e.g., releasing the mouse click) so that this point 53b here comes to coincide with 53. A corresponding change in the navigation polygon NP toward a new geometry P3 with the corner points 53, 50c, 52c and 51c is directly discernible from the figure. On the basis of the search for the most similar possible values on the other axes 30, 31 and 32, the characteristic values depicted there are practically unchanged as dose values although they are part of another solution which includes the characteristic value 53 which was not previously included by polygon P2. Thus in the variety of problem solutions in the database 1 there was already a solution which would permit a minimum dose burden of 25 gy on the spinal cord scale $h_3$ (axis 33) with reasonable burdens for the other risk organs $h_1$ and $h_2$ accordingly although the radiation burden for the target T is still too low, at approximately 75 gy.

The transition from FIG. 7 to FIG. 8 will be described in words here with regard to another functionality that is difficult to display graphically. Whereas in the transition from FIG. 6 to FIG. 7 an essentially sudden change in the polygon from FIG. 6 to the new navigation polygon P2 was assumed, the change in the polygon from P2 to P3 is provided with an alternative form of display which may also be used for all changes in the polygons, just like the sudden change is also possible for all individual steps.

A steady or continuous change in one polygon to the next polygon functions so that the user is able to visually experience or observe how a polygon P2 changes on the whole starting from a "distorted" point 53b to point 53. The two lines starting from point 53 begin from the old polygon P2 starting at point 53 and changing over to the lines of the new polygon, which is equivalent to a type of blurring effect or a steady transition effect which should take place so long that it is also visually perceptible. In a transition phase, the first stationary display of FIG. 7 changes to the second steady-state display of FIG. 8.

All the visual lines of the polygon P2 within the planning zone 40 are cross-faded from the left into all the lines of the polygon P3. The time of this cross-fading is a transition phase in which not only one solution from the database but instead two sections of two problem solutions are displayed from the database simultaneously but not completely and instead portions are being changed continuously.

A distortion of point 53b in the other direction (toward 53a) causes the blurring effect to begin in reverse at point 52b (from the right).

The technical function of the cross-fade ensures easier graphic comprehensibility by the user and gives the feeling of direction and quality of change without having to switch back to the previous old point again each time in order to detect the difference by a back-and-forth movement of points 53 and 53b.

A further improvement should not be desirable from FIG. 8 and should be an increase in the dose on the target scale as illustrated in FIG. 9 where at first unchanged corner points of the polygon P3 are shown. These are changed because before any other change in other corner points other than that on axis 33 a blocking of reverse steps on the $h_3$ axis which has just been optimized should be blocked.

This blocking is achieved by clicking on the section 33a, which is assigned to the axis 33. According to the diagram in FIG. 5, the corresponding regions can then also be found on the other axes, namely regions 31a, 32a and 30a, each assigned to the end of the scale, which indicates an exacerbation in order to illustrate the target direction of the improvement with the arrows shown symbolically at the other end.

Clicking on the sensitive area of the image 33a blocks values that are inferior to those already optimized with the setting 53 as the characteristic value for a respective radiation dose. This yields a change in the planning zone 40 because now this excludes all problem solutions which have dose values on the scale 33 that are between the point 53 and the maximum possible point of the upper end of the acceptance interval $a_{33}$ of FIG. 6. After activation of the blocking function, these values are shown with a different color in the diagram according to FIG. 9 with a light gray background here while the other (the remaining) planning zone still has the same color with respect to the environment.

This is shown more clearly in FIG. 5 where a first masked-out section 41 is obtained above the two connecting distances 64 and 61 which extend to the adjacent axes from the fixed point 53. The masked-out area 41 extends up to the edge of the polygon $P_a$ and also includes sections in the other zones of the polygon 40 because of the blocked characteristic values in this area, namely on the side which has most of the remaining planning zone 42. The cause of this is the fact that problem solutions with dose values on the axis 33 also extend with other dose values to the other axes 30, 32 and 31 into such regions with can no longer be maintained there. An overall solution with four characteristic dose values that belong together will now be blocked already if it has a point as a characteristic value which is higher in value than the point 53 on the axis 33.

This therefore yields a reduced planning zone 42 which comes to lie within a new outer outline $P_a'$ as shown on a larger scale in FIG. 5 and as characterized in FIG. 9 by a difference in gray value coverage. This also results in a new inner edge line $P_i'$ which is situated mainly on the right side of FIG. 5, while the new outer borderline $P_a'$ comes to lie mainly in the left area. However, this depends on which of the shiftable characteristic values 50 through 53 is selected for fixation or for a holding function. The corresponding assignment is easily visible from the description given above and a possible rotation of the diagram according to FIG. 5 to the right or to the left.

It is self-evident that the blocked region 41 can also be activated when the locking function is activated again by clicking on the section 33$a$ of the image in FIG. 9 in the sense of a toggle function so as to again yield a diagram like that in FIG. 8. Several points may also be fixed in the polygon based on the scalar values 50$c$, 52$c$ and 51$c$ in FIG. 9 which then reduce additional sections from the planning zone to arrive at a further reduced planning zone.

For the following description, a further improvement on the T axis 30 derived therefrom in FIG. 9 is also assumed. The dose for the target is still too low according to the characteristic value representation 50$c$. Therefore, a shift is performed in the direction of the arrow assigned to this axis, resulting in FIG. 10, where point 50$c$ is placed on point 50, the locking function of the axis $h_3$ is retained, i.e., the point 53 is determined.

FIG. 10 is then formed with or without a fluid transition, having a new point geometry 53, 50, as described above, and having points 51$d$ and 52$d$ corresponding to points 51 and 52 in FIG. 5. This yields polygon P1 as a navigation body as already depicted in FIG. 5. This solution which has been found and is represented by the polygon P1 corresponds to a found optimum at which although the $h_2$ axis is definitely worse in comparison with that in FIG. 9, the $h_1$ axis nevertheless remains unchanged and the $h_3$ axis has been minimized and the target axis 30 has been optimized to the best possible optimum 50 (corresponding to a value of 75 gy).

The control values for a radiation therapy plan corresponding to these settings, i.e., the solution thus found can be used subsequently for therapeutic purposes after being transmitted over the control lines 6, 7 into the therapy device, corresponding to a selection of controlled variables for the setting of the radiation head at the different instrument angles $\alpha_1$ and thus also corresponding to a predetermined intensity distribution as shown schematically in FIG. 3$a$ with three different directions, but retaining radiation influences from five different directions for the example described here on the basis of FIG. 2 in combination with corresponding intensity settings according to FIG. 2$a$ through 2$e$.

FIG. 6 $ff$ described here thus also contain archiving functions 75 and monitoring functions 70, as explained in conjunction with FIG. 5, these functions corresponding to a recording command, a playback command or a sequence of navigation polygons NP recorded previously. To do so with a corresponding click on the visual areas on the display screen by means of the handling instrument and the corresponding mouse cursor, pointers to certain problem solutions are stored temporarily. The storage of current navigation polygons which are to be eliminated again for a subsequent reconsideration, takes place with the store area on the display screen 3. If at least one navigation polygon NP is stored via the store region, then by clicking the "view" section of the function area 75, it is possible to switch to displaying stored functions. The storage and/or referencing take place through the pointer described here to the database set which is one of the problem solutions stored in memory 1. This storage may be done in the form of a first log data file and when a view area is clicked on the screen 3 the planning tool changes, i.e., the screen display on the display screen 3 changes in the view mode and chose the respective navigation polygons NP which were previously selected via the store area. The corresponding design of the respective planning zone 40 or only 42 (minus section 41) is displayed accordingly.

It is possible to move forward or backward within the log data file by using the recorder button in section 70 of the screen display. In this way new starting points for new optimization searches can be selected, corresponding to a solution discovered previously, stored temporarily before wanting to perform further optimization in a direction which was assumed at that time to be reliable, which would then not lead to any reasonable result. It is helpful here to return to the previously stored starting point as the NP.

In addition to the one log data file described here, a sequential log data file may also be carried along automatically, tracking each development step of the NP in the planning zone and recording the results so that by forward and backward switching and beginning and end switching areas in the function section 70, it is possible to achieve a control. This facilitates retrieval of problem solutions seen previously.

Although first a point of emphasis on the section depicted in FIG. 5 of a display screen has previously been set, the respective secondary information which is also depicted should not be disregarded. This is shown by the isodose display which is now closer to reality than the very abstract hypothetical model of the planning zone used previously and is also show by the dose-volume display in the two diagrams visible at the left in FIG. 6. The polygon display NP marked in the global planning zone 40 is the starting point and creates an easy optical visualization of the visualization of isodoses and volume histograms which are known per se as such, such a visualization also being available and familiar to the user.

A physical therapy setup is also stored in the background and may if necessary be included in a physical planning window under "information."

Although the display according to FIG. 5 preferably works two-dimensionally, the two-dimension display can also be expanded into the third dimension in the isodoses by different transverse sections. Likewise the dose/volume histogram display according to FIG. 11 is also capable of clearly transferring the planar representation of FIG. 5 to the third dimension for the user, whereby the dose is plotted on the abscissa and the respective volume fraction is plotted on the ordinate. For example, the dose/volume distribution is depicted as a $dV_T$ graph, which is designed so that the desired dose of 80 gy is achieved in 65% of the volume of the target T, while 35% is exposed to a lower dose. The limit values $RW_{max}$ for the risk are and $RW_{min}$ for the target as defined above are plotted on the horizontal axis; this shows that a curve of $dV_R$ is obtained for the organs (the risk volumes) and this curve is much less than 20%, namely 10% above the maximum value of the radiation burden.

On the basis of the representation as volume, the third dimension is also depicted in this graph. The isodose representation is one of a plurality of possible two-dimensional cuts. A strictly two-dimensional representation in the planning zone 40 is the starting point for the two auxiliary representations described above.

We claim:

1. A planning tool for interactive selection of control variables of a radiation therapy plan from a database (1) having a plurality of previously calculated or predetermined solutions, whereby each solution
   (i) represents a radiation therapy plan comprising a plurality of control variables or commands, adapted to be sent to a radiation therapy device or to be made available to this therapy device, at a point in time prior to applying the control variables or commands as part of a performing the therapy; and
   (ii) contains characteristic values of radiation doses for a target volume (T) and at least one risk volume stored in the database (1);
   and whereby
   (a) several axes are one of plotted and visually displayed on a display device, said several axes provided as radiation dose scales for the target volume (T) and the at least one risk volume, representing at least one risk axis and one target axis, whereby no axis, coincides with another axis and adjacent axes do not extend in parallel;
   (b) the characteristic values of the radiation doses for at least a plurality of the stored solutions are assigned to the particular axes respectively thereby obtaining an acceptance interval for each risk axis and the target axis (30), the acceptance intervals jointly defining a planning zone for all axes; and
   (c) the planning zone on the display device (3) is one of emphasized with respect to an environment and displayed in a visual manner with respect to the environment outside the planning zone.

2. The planning tool according to claim 1, whereby each axis (30 to 33) has a section as an acceptance interval which is within the planning zone (40) and each section has an upper and lower boundary value (30m, 30n).

3. The planning tool according to claim 1, whereby the planning zone has a polygonal shape as the planning area with an inner and outer boundary polygon ($P_i$, $P_a$).

4. The planning tool according to claim 1, whereby connecting distances of interval ends or the marginal values of adjacent axes (30, 32) define an inner and an outer border of the planning zone for perceptible visualization of the multitude of solutions stored in the database.

5. The planning tool according to claim 1, whereby only one solution is displayed from the database within the planning zone in the state of a first stationary display so that its characteristic values for radiation doses on the axes are connected by visible lines to form a navigation line body.

6. The planning tool according to claim 5, whereby all the connecting lines are within the planning zone (40).

7. The planning tool according to claim 5 whereby the connecting lines are linear to form a polygon (P1) as a navigation line body having the same number of corners as a number of outer corners (Pa, Pa') of the planning zone (40).

8. The planning tool according to claim 5, whereby in a transitional state from the first stationary representation to a second stationary representation (50c through 53c) a form or a position of the first line body (NP) changes and forms a second line body (P3) but remains within the planning zone (40) for displaying a second solution from the database with its respective characteristic values for radiation doses of target volumes and multiple risk volumes.

9. The planning tool according to claim 8, whereby during the transitional state there is a change from the first line body (P2) to the second line body (P3) as a fluid or gradual transition in order to visualize and display the change and two solutions or respective line bodies (P3, P2) are each displayed simultaneously in at least some sections in the visible fluid change.

10. The planning tool according to claim 1, whereby each solution represents a plurality of dose distributions for multiple angle positions suitable for a radiation head (12) of the therapy device.

11. The planning tool of claim 10, wherein the therapy device has multiple strips (13,14) of a multileaf collimator in front of the radiation head.

12. The planning tool according to claim 1, whereby only a single solution of the plurality of stored solutions is represented in the planning zone (40), which is set off from the background (45a, 45) in particular to differentiate by color or by the gray value, during a stationary display.

13. The planning tool according to claim 1, whereby a first section (41) of the planning zone is blocked or can be blocked in order to leave the remaining planning zone (42) for changes in the navigation body (NP) that has been entered.

14. The planning tool according to claim 13, whereby the blocking is canceled again in order to add the first section (41) to the remaining section for changes in the navigation body input.

15. The planning tool according to claim 13, whereby the blocking of the first section takes place by blocking a characteristic value (53) on one of the axes (33), so that the characteristic value (53) becomes a crown point and forms a new corner of a new outer polygon ($P_a'$) and certain solutions of the database are blocked
   (i) for display as a navigation line body (NP) and
   (ii) for selection,
   where the certain solutions have a characteristic value as a characteristic dose value on one axis (33) which is in the blocked section (41).

16. The planning tool according to claim 1, whereby the characteristic values (50, 51, 52, 53) of the radiation doses are represented by EUD values as average dose distributions per organ or per target.

17. A Planning tool for interactive selection of control variables of a radiation therapy plan from a database (1) having a plurality of previously calculated or predetermined solutions,
   whereby each solution
   (i) represents a radiation therapy plan which itself consists of a plurality of controlled variables or commands to be one of sent (6,7) to a radiation therapy device (10,11,13) and made available for the therapy device;
   (ii) contains at least one characteristic value of a radiation dose for a target volume (T) and at least one risk volume, said characteristic values being stored in the database (1) so that they are available at least two-dimensional representations;
   and whereby
   (a) multiple axes are one of plotted and displayed visually as radiation dose scales on a display device to form a risk axis and a target axis, whereby no axes coincide and whereby adjacent axes are not parallel;

(b) a planning zone on the display device is one of emphasized in comparison with an environment and represented visually, so that it can be distinguished from a surrounding area, whereby the planning zone being defined by combining all solutions of the database (1), and one of the plurality of solutions in the planning zone is emphasized with respect to the planning zone.

18. A planning tool for an interactive selection of control variables of a radiation therapy plan from a database (1) having a plurality of previously calculated solutions, whereby each solution
  (i) represents a radiation therapy plan which comprises a plurality of control variables or commands which can be sent (6, 7) to a radiation therapy device or made available for this device (10);
  (ii) contains one characteristic value of a radiation dose for a target volume and at least two comparable characteristic values for at least two risk volumes which characteristic values are stored in the database (1);
  whereby the characteristic values are assigned to the axes respectively for at least a plurality of the stored solutions, so that for at least two risk axes acceptance intervals are obtained, jointly defining a planning zone for risk all axes.

19. A Planning method of controlling a visually perceptible representation for the selection of at least one section of a radiation therapy from a database of multiple possible solutions, whereby each of the solutions includes a plurality of control settings of a radiation device, used for radiation therapy, wherein
  (i) multiple radiation dose scales of a target or risk organs are one of plotted in a star shape and displayed graphically;
  (ii) from available solutions stored in advance in the database (1, 1*a*), an acceptance interval is plotted on each of the rays of the star, whereby each acceptance interval has an upper and a lower boundary value;
  (iii) by directly connecting the boundary values of acceptance intervals on neighboring scales or neighboring rays, a global planning horizon is outlined as a planning zone for perceivable visualization of a multitude of solutions available in the database.

20. Method according to claim 19, characterized in that arrow points on the rays of the star point in the direction of an increasing dose in the case of targets and in the direction of a decreasing dose in the case of risk areas ($h_1$, $h_2$).

21. Method according to claim 19, whereby the dose values of only one solution from the database (1) are characterized in points in the corresponding acceptance intervals and are or will be connected essentially in a straight line to form a navigation polygon (NP) which depicts a solution from the database in a cohesive visual form.

22. Method according to claim 21, whereby a transition from one navigation polygon (NP=P2) to a following navigation polygon (P3) is fluid, with intermediate states being displayed.

23. Method according to claim 19, characterized in that after pulling with a pointer on an operating device (4) at a location in the navigation polygon, in particular a corner of the polygon along the respective ray (33) and within the corresponding acceptance interval ($a_{33}$) the current navigation polygon (P2) is masked out and then the navigation polygon (P3) which visualizes a solution in the database whose weighting in the current acceptance interval comes closest to the displaced point of the navigation polygon is faded-in and in particular its characteristic values in the other acceptance intervals at the same time have the lowest possible deviation from the points previously depicted on the rays of the preceding navigation polygon.

24. The method of claim 19 wherein marking elements are assigned to the rays of the (radiation dose scales forming rays of a star shape to cause blocking of the particular section of the acceptance interval of the respective ray from a worst edge point to a displayed corner point of the navigation polygon.

25. Method according to claim 24, whereby by operating with a mouse pointer a previously already operated marking element (33*a*), the respective blocked section of the acceptance interval or planning horizon, is released again in order to be able to select the respective solutions from the database again and display their visualizations as being added to the current planning horizon.

26. Method according to claim 24 whereby the blocking of the first section (41) takes place by blocking the inferior scale values which are based on the dose and dose direction on the respective axis (30 to 33).

27. Method according to claim 19, characterized in that by clicking or operating a marking element (33*a*, 31*a*), a section of the corresponding acceptance interval ($a_{33}$) is blocked or can be blocked.

28. Method according to claim 27, whereby after blocking, only those solutions which are outside of the blocked section (41) of the planning zone can be selected in a reduced planning zone (42) and at least one boundary value (30*n*, 30*m*) of one of the acceptance intervals of the other of the dose scales is altered.

29. Method according to claim 28, whereby the restricted planning zone (42) is displayed with an emphasis as a planning horizon part in comparison with the masked-out first planning horizon part (41) whereby the two parts added up yield the planning zone.

30. Method according to claim 29, whereby multiple sections of multiple axes can be blocked in order to block multiple sections of the planning horizon, leaving a further reduced remaining planning horizon part.

31. Method according to claim 19, whereby a navigation polygon is provided, said navigation polygon being depicted in different ways visually within the planning zone, and a distribution of radiation doses, in particular according to EUD values on risk organs and/or the target (T, $h_1$, $h_2$, $h_3$) being given as the dose distribution polygon.

32. Method according to claim 19, whereby storage of a number of the currently displayed solutions in the current navigation polygon (P1) is initiated by operating a limited control section (75) that is displayed.

33. Method according to claim 32, whereby by operating another limited control section (75), it is possible to switch the display to a visual mode to show the solutions from the database (1) for the stored numbers for display (3, 3*a*), said solutions having been stored using the first control section of the display screen (3).

34. Method according to claim 33, whereby with the help of recorder sections (7) on the visible screen, the visualizations corresponding to the respective stored solutions are or can be displayed according to the user's wishes.

35. Method according to claim 33 whereby the operation of a previously operated control section triggers a switching to a mode which allows continuation of the navigation in the current planning zone.

36. Method according claim 32 whereby the operation involves clicking with a mouse pointer or touching a display screen at a specific location on the screen (3).

37. Method according to claim 19, whereby solutions, in particular pointers to stored data records of the database are automatically stored sequentially in a log data file (5, 1) in a background, said solutions being assigned to a navigation polygon (P2) currently being displayed.

38. Method according to claim 37, whereby the operation of one or more recorder image sections (70) whose functions correspond to recorder functions the visualizations of the solutions referenced in the log data file, which are and/or can be retrieved according to the user's requirement.

39. Method according to claim 19 whereby in a second stationary display another line body (NP) is depicted with characteristic values (50c through 53c) as corners, its corners having the lowest possible deviation on the whole in comparison with the line body depicted in the first stationary state and/or the second line body (P3) is the line body closest to the corner points that were not shifted and/or a new solution is displayed as a line body whose corner points that have not been actively shifted have the least possible deviation from the corner points represented previously.

40. A Planning tool for interactive selection of an object design or controlled variables from a database (1) having a plurality of previously calculated or predetermined solutions, whereby each solution
  (i) having a plurality of controlled variables or commands sent (6, 7) to an operating device (10,11,13) or made available for this device (10); or
  (ii) has technical parameters which one of describe and determine the technical properties of the object to be designed;
  and whereby
  (a) multiple axes are plotted or displayed visually with scales for characteristic values of the solutions on a display device to form axes for properties, whereby no axes coincide and adjacent axes do not run in parallel;
  (b) characteristic values for at least a plurality of the stored solutions are assigned to the respective axes in such a way that there is for each axis an acceptance interval together defining a planning zone for all axes;
  (c) the planning zone is emphasized in comparison with environment on the display device or is displayed in a visually different outline.

41. The planning tool according to claim 40, whereby each axis (30 to 33) has a section as an acceptance interval which is within the planning zone (40), and each section has an upper edge value and a lower edge value (30m, 30n).

42. The planning tool according to claim 40 whereby connecting distances of interval ends or the edge values of adjacent axes (30, 32) define an outer border and an inner border of the planning zone for perceptible visualization of the multitude of solutions stored in the database.

43. The planning tool according to claim 40 whereby in the state of a first stationary display only one solution from the database is displayed within the planning zone so that the characteristic values (50, 51, 52, 53; 50b through 53b) are connected with visual lines as technical properties on the axes (30 through 33) to form a navigation line body (NP, P1, P2).

44. The planning tool according to claim 43, whereby a form or position of the first line body (NP) changes in a transition state from a first stationary display to a second stationary display (50c through 53c), and a second line body is formed (P3) but remains within the planning zone (40) for displaying a second solution from the database with its respective technical characteristic values.

45. The planning tool according to claim 44, whereby during the transition state there is a morphing or gradual change from the first line body (P2) to the second line body (P3) in order to make the change visual and visible, and two solutions or the respective line bodies (P3, P2) are each displayed visually and simultaneously at least part time during the visibly morphing change.

46. The planning tool according to claim 40 whereby in the planning zone (40) which is differentiated by color or in terms of the gray value from the background (45a, 45), only a single solution of the plurality of stored solutions is displayed during a state of a stationary display.

47. The planning tool according to claim 40 whereby a first section (40) of the planning zone is blocked or can be blocked (30a through 33a) to leave the remaining planning zone (42) for changes in the navigation body (NP) entered.

48. The planning tool according to claim 47, whereby the blocking can be canceled again in order to add the first section (40) to the remaining section for changes in the navigation body entered.

49. The planning tool according to claim 47, whereby the blocking of the first section takes place by blocking a property value (53) on one of the axes (33) so that the characteristic value (53) becomes a crown point and a new corner of a new outer polygon (P$_a$') is formed and certain solutions of the database are blocked
  (i) for a display as a navigation line body (NP) and
  (ii) for a selection,
  whereby the certain solutions have a characteristic value as a property value on the one axis (33) which is in the blocked section (41).

50. A Planning tool for interactive selection of an object design or control variables of a device from a database (1) having a plurality of previously calculated or predetermined solutions, whereby
  (a) multiple axes for properties of the device or object are plotted or displayed visually on a display device whereby the axes do not coincide and adjacent axes do not run in parallel;
  (b) characteristic values of properties for at least a plurality of the stored solutions are assigned to the respective axes so that acceptance intervals are formed together defining a planning zone on the display device for all axes;
  (c) the planning zone is one of displayed as emphasized in comparison with an environment and therefore visually distinguishable from the environment.

* * * * *